(12) United States Patent
Slater et al.

(10) Patent No.: US 8,573,048 B2
(45) Date of Patent: Nov. 5, 2013

(54) METHOD AND APPARATUS FOR ANALYING FRACTURE FLUIDS IN A DRILLING OPERATION

(75) Inventors: Kenneth Slater, Houston, TX (US); Robert P. Schlemmer, Kuala Lumpur (MY)

(73) Assignee: M-I L.L.C., Houston, TX (US)

( * ) Notice: Subject to any disclaimer, the term of this patent is extended or adjusted under 35 U.S.C. 154(b) by 858 days.

(21) Appl. No.: 12/530,681

(22) PCT Filed: Mar. 12, 2008

(86) PCT No.: PCT/US2008/056704
§ 371 (c)(1), (2), (4) Date: Jan. 27, 2010

(87) PCT Pub. No.: WO2008/112795
PCT Pub. Date: Sep. 18, 2008

(65) Prior Publication Data
US 2011/0130965 A1     Jun. 2, 2011

Related U.S. Application Data

(60) Provisional application No. 60/894,373, filed on Mar. 12, 2007.

(51) Int. Cl.
*E21B 47/10* (2012.01)
(52) U.S. Cl.
USPC .......................... 73/152.18; 73/152.01; 73/38
(58) Field of Classification Search
USPC ............... 73/152.18, 152.01, 152.23, 152.38, 73/61.62
See application file for complete search history.

(56) References Cited

U.S. PATENT DOCUMENTS

| | | | | |
|---|---|---|---|---|
| 4,506,542 A | * | 3/1985 | Rose | 73/38 |
| 4,748,849 A | | 6/1988 | Jamison et al. | |
| 4,876,013 A | * | 10/1989 | Shmidt et al. | 210/650 |
| 5,488,224 A | * | 1/1996 | Fagan et al. | 250/227.16 |
| 5,987,969 A | | 11/1999 | Joseph et al. | |
| 6,055,874 A | * | 5/2000 | Onan et al. | 73/865.6 |
| 6,105,415 A | | 8/2000 | Kenney | |
| 6,330,826 B1 | | 12/2001 | Meeten | |
| 6,581,440 B1 | | 6/2003 | Rupieper | |
| 7,051,807 B2 | * | 5/2006 | Vinegar et al. | 166/245 |
| 7,549,320 B2 | * | 6/2009 | Funkhouser et al. | 73/37 |
| 7,900,504 B2 | * | 3/2011 | Huynh et al. | 73/61.41 |
| 2008/0236891 A1 | * | 10/2008 | Huynh et al. | 175/48 |
| 2009/0308656 A1 | * | 12/2009 | Chitwood et al. | 175/40 |

OTHER PUBLICATIONS

International Search Report, mailed Jul. 21, 2008, for PCT/US2008/056704.

* cited by examiner

*Primary Examiner* — Hezron E Williams
*Assistant Examiner* — Rodney T Frank
(74) *Attorney, Agent, or Firm* — Patents+TMS, P.C.

(57) ABSTRACT

An apparatus for testing a drilling fluid includes a vessel having a fluid inlet, a fluid outlet, and a pair of opposed impermeable platens disposed within the vessel. The apparatus further includes a test fluid container in fluid communication with the fluid inlet, and a collection container in fluid communication with the fluid outlet. Additionally, the system includes a data acquisition device configured to receive data from at least one of the vessel, the test fluid container, and the collection container. Also, a method for determining sealing characteristics of a drilling fluid includes injecting a test fluid having a fluid loss control material from a test fluid container to a vessel, the vessel having a first impermeable platen and a second impermeable platen with a gap between the two platens. The methods further includes measuring a fracture tip fluid loss through the gap.

22 Claims, 7 Drawing Sheets

METHOD AND APPARATUS FOR ANALYING FRACTURE FLUIDS IN A DRILLING OPERATION

BACKGROUND

1. Field of the Disclosure

The present disclosure generally relates to systems and methods for testing drilling fluids for drilling operations. More particularly, the present disclosure relates to methods and systems for determining sealing characteristics of fluid loss control materials and optimizing drilling fluids using such particles.

2. Background Art

During the drilling of a wellbore, various fluids are typically used in the well for a variety of functions. The fluids may be circulated through a drill pipe and drill bit into the wellbore, and then may subsequently flow upward through wellbore to the surface. During this circulation, the drilling fluid may act to remove drill cuttings from the bottom of the hole to the surface, to suspend cuttings and weighting material when circulation is interrupted, to control subsurface pressures, to maintain the integrity of the wellbore until the well section is cased and cemented, to isolate the fluids from the formation by providing sufficient hydrostatic pressure to prevent the ingress of formation fluids into the wellbore, to cool and lubricate the drill string and bit, and/or to maximize penetration rate.

In most rotary drilling procedures the drilling fluid takes the form of a "mud," i.e., a liquid having solids suspended therein. The solids function to impart desired rheological properties to the drilling fluid and also to increase the density thereof in order to provide a suitable hydrostatic pressure at the bottom of the well. The drilling mud may be either a water-based or an oil-based mud.

Drilling muds may consist of polymers, biopolymers, clays and organic colloids added to a water-based fluid to obtain the required viscosity and filtration properties. Heavy minerals, such as barite or calcium carbonate, may be added to increase density. Solids from the formation are incorporated into the mud and often become dispersed in the mud as a consequence of drilling. Further, drilling muds may contain one or more natural and/or synthetic polymeric additives, including polymeric additives that increase the rheological properties (e.g., plastic viscosity, yield point value, gel strength) of the drilling mud, and polymeric thinners and flocculents.

Polymeric additives included in the drilling fluid may act as fluid loss control agents. Fluid loss control agents, such as starch, prevent the loss of fluid to the surrounding formation by reducing the permeability of filter cakes formed on the newly exposed rock surface. In addition, polymeric additives are employed to impart sufficient carrying capacity and thixotropy to the mud to enable the mud to transport the cuttings up to the surface and to prevent the cuttings from settling out of the mud when circulation is interrupted.

As such, many drilling fluids may be designed to form a thin, low-permeability filter cake to seal permeable formations penetrated by the drill bit. The filter cake is essential to prevent or reduce both the loss of fluids into the formation and the influx of fluids present in the formation. Upon completion of drilling, the filter cake may stabilize the wellbore during subsequent completion operations such as placement of a gravel pack in the wellbore. Filter cakes often comprise bridging particles, cuttings created by the drilling process, polymeric additives, and precipitates. One feature of a drilling fluid is to retain these solid and semi-solid particles as a stable suspension, free of significant settling over the time scale of drilling operations.

Once the drilling fluid is lost into the formation, it becomes difficult to remove. Calcium and zinc-bromide brines can form highly stable, acid insoluble compounds when reacted with the formation or substances contained therein. This reaction may reduce the permeability of the formation to any subsequent out-flow of the targeted hydrocarbons. The most effective way to prevent such damage to the formation is to limit fluid loss into the formation.

Thus, providing effective fluid loss control is highly desirable to prevent damaging the formation in, for example, completion, drilling, drill-in, displacement, hydraulic fracturing, work-over, packer fluid emplacement or maintenance, well treating, or testing operations. In certain drilling environments, the formation may be exceptionally prone to damage from fluid loss. Examples of such drilling operations may include depleted zone drilling.

Depleted drilling zones may be especially prone to fractures (i.e, cracks and disruptions in a formation that may be either naturally formed or induced). Fracturing during the drilling operation, also known as induced fracturing, typically occurs in permeable rocks such as sandstone and carbonates or within impermeable rock typified by shale formations. Induced fracturing is of particular concern when drilling into depleted zones where a drop in pore pressure is anticipated as the reserves decline. In these situations, drilling then becomes more of a technical challenge as the mud weight required to support a section may exceed the tensile strength, or fracture resistance, of the formation. This in turn could lead to increased drilling fluid losses and increased well costs.

Large-scale core testing of fracturing is costly and time consuming. Consequently, there exists a need for a reproducible test and laboratory-scale equipment that can effectively mimic a fracture so that lost circulation materials and lost circulation material blends can be evaluated prior to or instead of large scale core testing.

Accordingly, there exists a continuing need for systems and methods of testing and optimizing drilling fluids and/or fluid loss control materials for drilling in permeable and impermeable formation.

SUMMARY OF THE DISCLOSURE

In one aspect, embodiments disclosed herein relate to an apparatus for testing a drilling fluid including a vessel having a fluid inlet, a fluid outlet, and a pair of opposed impermeable platens disposed within the vessel. The apparatus further includes a test fluid container in fluid communication with the fluid inlet, and a collection container in fluid communication with the fluid outlet. Additionally, the system includes a data acquisition device configured to receive data from at least one of the vessel, the test fluid container, and the collection container.

In another aspect, embodiments disclosed herein relate to a method for determining sealing characteristics of a drilling fluid including injecting a test fluid having a fluid loss control material from a test fluid container to a vessel, the vessel having a first impermeable platen and a second impermeable platen with a gap between the two platens. The methods further including measuring a fracture tip fluid loss through the gap.

In another aspect, embodiments disclosed herein relate to an apparatus for testing the seal characteristics of a drilling fluid including a vessel. The vessel has a fluid inlet, a fluid outlet, a first platen disposed within the vessel and a second platen disposed within the vessel, wherein the first and second platens are disposed to create a gap separated by a predetermined minimum distance. The apparatus further includes a test fluid container in fluid communication with the fluid inlet and a collection container in fluid communication with the fluid outlet. Additionally, the system includes a data acquisition device configured to receive data from at least one of the vessel, the test fluid container, and the collection container.

Other aspects and advantages of the disclosure will be apparent from the following description and the appended claims.

DETAILED DESCRIPTION

The present disclosure generally relates to systems and methods for testing drilling fluids for drilling operations. More particularly, the present disclosure relates to methods and systems for determining sealing characteristics of fluid loss control materials and optimizing drilling fluids using such particles.

Embodiments of the present disclosure described herein include a testing system for determining the sealing characteristics of drilling fluids, including both oil- and water-based fluids, as may be used in drilling earth formations. The types of formations discussed below generally include permeable formations such as sandstone and carbonates, however, the present disclosure may also find use when testing drilling fluids used while drilling impermeable formations such as shale. Those of ordinary skill in the art will appreciate that the type of formation being tested and the specific fluids discussed below are not a limitation on the scope of the present disclosure. As such, all discussed examples are merely exemplary, and the systems of testing and methods of determining sealing characteristics and optimizing drilling fluids are exemplary as well.

Figure 1:
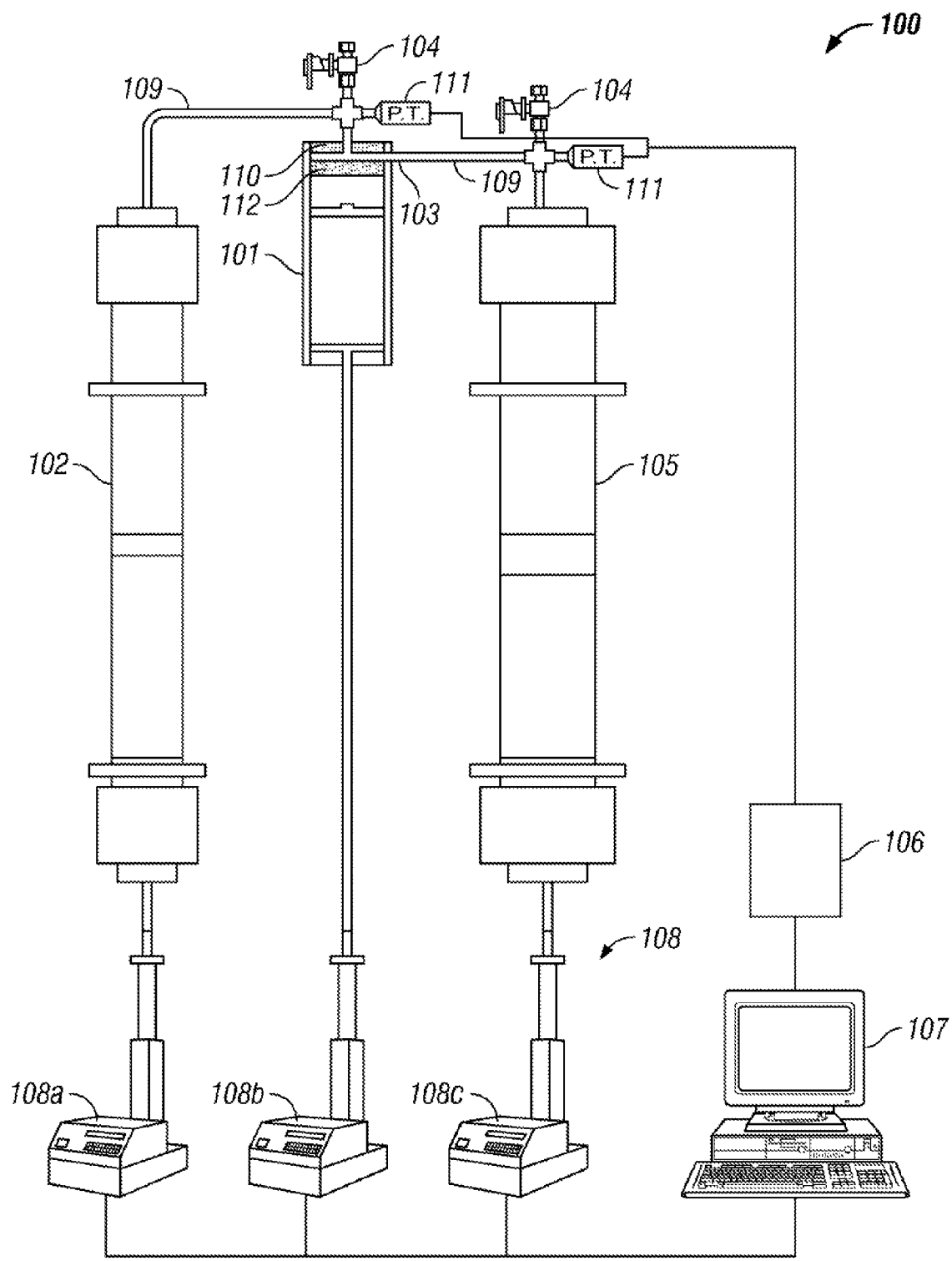
FIG. 1 shows a system for testing a drilling fluid in accordance with embodiments of the present disclosure.

Referring to FIG. 1, a system 100 for testing a drilling fluid in accordance with embodiments of the present disclosure is shown. In this embodiment, system 100 includes a testing vessel 101 and a fluid container 102. System 100 also includes a data acquisition system 106, a computer 107, and a series of pumps 108.

More specifically, system 100 includes a test fluid container 102 in fluid communication with vessel 101. Container 102 may include any type of containers used to contain drilling fluid, and as such, may include plastic, steel, aluminum, or composite containers. Those of ordinary skill in the art will appreciate that because the system is pressurized, the containers must be able to handle the requisite pressure requirements of system 100. Likewise, the fluid connections providing fluid communication between container 102 and vessel 101 must also be able to handle pressure requirements of the system, and as such, appropriate fluid lines 109 may include steel lines, reinforced plastic lines, and other lines as known to those of ordinary skill in the art.

In this embodiment, a mud pump 108a is used to pressurize system 100 by providing a pressure to test fluid container 102. A test fluid is stored in test fluid container 102. Mud pump 108a is used to deliver the test fluid, as required by the testing operation, to vessel 101. In one aspect, mud pump 108a may include a syringe pump, however, those of ordinary skill in the art will appreciate that other types of pumps may be used to inject a fluid from container 102 to vessel 101.

In one embodiment, mud pump 108a applies pressure to the test fluid container 102 such that the test fluid is delivered to the vessel 101 at a constant flow rate in the range of 0.25 to 1.0 mL/minute. In one embodiment, the mud pump 108a applies a pressure sufficient to supply the test fluid to the vessel 101 at a constant flow rate of about 0.5 mL/minute.

A collection container 105 is used to collect a fluid from vessel 101 during the testing. Collection container 105 may also include any type of container used to hold drilling fluids, and as such, may include steel or plastic containers. Collection container 105 is also fluidly connected to vessel 101 via fluid lines 109, as described with respect to container 102 above. In this embodiment, a tip pump 108c provides a back pressure to the fracture tip 103 of vessel 101. In one aspect, tip pump 108c may include a syringe pump, however, other pumps may be used that create a back pressure to the fracture tip 103, as described above. In one embodiment, the tip pump 108c applies a back pressure to the fracture tip 103 in the range of 20 to 30 psi. In one embodiment the tip pump 108c applies a back pressure to the fracture tip of about 25 psi.

A closure pump 108b is connected to vessel 101 to control a fracture width of a pair of opposed platens 110 and 112 disposed in vessel 101. In this embodiment, closure pump 108c provides a constant confining pressure to vessel 101. In one embodiment, closure pump 108b applies a confining pressure in the range of 100 to 500 psi. In one embodiment, closure pump 108b applies a confining pressure of about 125 psi. In one aspect, third pump 108c may include a syringe pump, however, other pumps may be used that provide a pressure to vessel 101 to control and/or measure a pressure inside vessel 101.

Those of ordinary skill in art will appreciate that in other systems, a single pump or other configurations of pumps may provide the requisite pressures to test a drilling fluid. As such, the precise configuration of pumps 108 described in FIG. 1 is not a limitation on the scope of the present disclosure.

System 100 also includes a plurality of sensors 111 that may be used to measure, inter alia, pressures, temperatures, densities, conductivities flow rates, flow levels, or other parameters of system 100 or of drilling fluids being tested. Thus, sensors 111 may be used to collect data or to determine a condition of system 100. In this embodiment, sensors 111 are operatively connected to data acquisition system 106. Data acquisition system 106 may include any device used to collect, document, or analyze data from system 100. Examples of data acquisition systems 106 that may be used in aspects of the present disclosure include analog-to-digital converters and digital-to-analog converters. Thus, embodiments in certain embodiments, data acquisition system 106 may receive a digital and/or analog input/output from sensors 111, pumps 108, or directly from another component of system 100, collect and/or analyze the data, and in certain embodiments, transfer the data to a computer 107 for further analyzing. Examples of methods of transferring the data from data acquisition system 106 to computer 107 may include, for example, via a USB (universal serial bus), parallel ports, serial communication ports, direct data acquisition plug-in boards, or remote terminal connections. Thus, in certain embodiments, data acquisition system 106 may be directly or indirectly configured to transfer data to computer 107.

Likewise, computer 107 may be used to send instructions to data acquisition system 106, sensors 111, pumps 108, or other components of system 100. Examples of such instructions may include instructions to control an operational parameter, such as, a pressure, a flow rate of a fluid, a distance between media plates, or instructions to request additional data from a component of system 100. Such instructions may be sent from computer 107 either through data acquisition system 106 or, in certain embodiments, directly to an individual component of system 100. Those of ordinary skill in the art will appreciate that computer 107 may be used to collect data, analyze data, and/or to control the testing.

Additionally, computer 107 may be used to render visual representations of collected and analyzed data. Visual representations may include the generation of data tables, numerical representations, graphical representations, or other forms of displaying data. Examples of such visual representations will be discussed in greater detail below.

Other components of system 100 may include a plurality of valves 104, which may be controlled via data acquisition system 106, computer 107, or otherwise manually actuated to control an operational parameter of system 100. Those of ordinary skill in the art will appreciate that any number of valves, valve types, and location of such valves will vary according to the design of system 100. However, generally, it may be beneficial to have valves in locations to control both the flow of fluids through system 100 and the pressure of portions of system 100. Furthermore, those of ordinary skill in the art will appreciate that other design variations to system 100 may be possible that include additional components such as, for example, multiple computers 107, data acquisition systems 106, multiple test vessels 101, additional fluid containers (not shown), or additional sensors 111 including other measuring devices.

While system 100 has been discussed generally above, the construction and components parts of vessel 101 will be discussed in detail below so that the operation and testing conditions system 100 provides for is more clearly understood.

Figure 2:
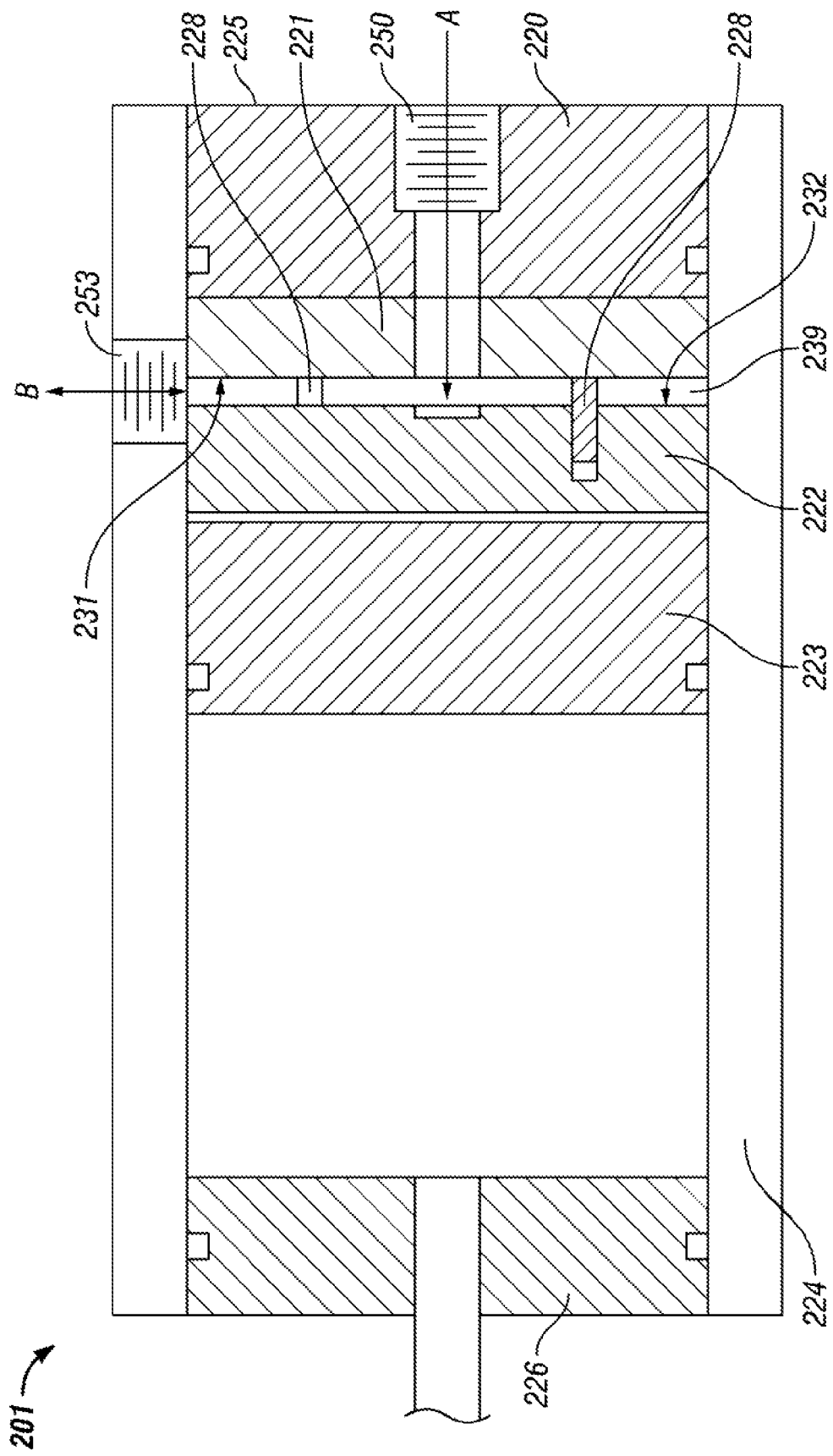
FIG. 2 shows a cross-section view of a vessel according to embodiments of the present disclosure.

Referring to FIG. 2, a cross-section view of vessel 201 according to embodiments of the present disclosure is shown. In this embodiment, vessel 201 includes a pressure chamber 224. Pressure chamber 224 is sealed on a first end 225 by an upper cap (not shown) and sealed on a second end 226 by lower cap (not shown). A material that may be used to construct pressure chamber 224, upper cap, and lower cap includes, for example, 4130 alloy steel. However, those of ordinary skill in the art will appreciate that other materials may be used that are both sealable and that withstand the pressure requirements of vessel 201. Examples of types of sealing engagement between upper cap, lower cap, and pressure chamber 224 include threadable and/or slidably engaging connections. In a threadable connection, an inner diameter of upper cap or lower cap may be configured to threadably engage an outer diameter of pressure chamber 224 to provide a sealed system that prevents the escape of fluids and gasses. In a slidably engaging system, pressure chamber 224 may include ratcheting ends (not shown) that slidably engage ratchet ends of upper cap or lower cap. To further enhance the sealability of vessel 201, thereby preventing the escape of gases and fluids therefrom, additional components may be used including, for example, one or more seals disposed along the outer diameter of pressure chamber 224. Those of ordinary skill in the art will appreciate that the method of constructing the body of vessel 201 is exemplary, and not a limitation on the scope of the present disclosure.

A first platen 221 is disposed adjacent a first support plate 220. A second platen 222 is disposed in pressure chamber 224 adjacent a second support plate 223. The geometry of the first and second platens 221 and 222 will be discussed in greater detail below. First and second support plates 220 and 223 are sealingly retained within the pressure chamber 224. First and second platens 221 and 222 are disposed opposed to each other in the pressure chamber 224, with a gap 229 formed therebetween.

Gap 229 defines the distance a first facing surface 231 on first platen 221 and a second facing surface 232 on second platen 222 are apart for a given test. The gap 229 is set a minimum distance for each test and may be adjusted so that each test is performed with a different, predetermined minimum distance between the first facing surface 231 and the second facing surface 232. The gap 229 is set to a minimum distance to model the typical fracture opening in a wellbore. In one embodiment the minimum gap 229 is set to a predetermined distance of 0 microns. In another embodiment, the minimum gap 229 is set to a predetermined distance between 0 and 1000 microns. In another embodiment, the minimum gap 229 is set to a predetermined distance between 0 and 2000 microns. In another embodiment, the minimum gap 229 is set to a predetermined distance between 250 and 1000 microns. In another embodiment, the minimum gap 229 is set to a predetermined distance between 250 and 1100 microns. In yet another embodiment, the minimum gap 229 is set to a predetermined distance of about 500 microns. Thus, in one test, gap 229 may be set so that the first and second platens 221 and 222 are substantially touching thereby forming a small gap, while in other tests, gap 229 may be set a specified distance apart, thereby forming a larger gap 229.

In one embodiment, a minimum gap 229 is set by adjusting at least one set screw 228 located in one of the first or second platens 221 or 222. In FIG. 2, set screws 228 are shown located in the second platen 222. One of ordinary skill in the art will appreciate that one or more set screws 228 may alternatively be located in the first platen 221. When one or more set screws 228 are used to adjust the gap 229 between the first and second platens 221 and 222, a measuring device, such as a micrometer may be used to measure the height of each set screw to determine the width of the gap 229. In another embodiment, a proppant is used to create the minimum gap 229. In this embodiment, a proppant, such as that used to prop open fractures in a wellbore, is placed between the first and second platens 221 and 222 to separate the opposing facing surfaces 231 and 232. Examples of proppant include sized marble, sand grains, resin-coated sand, and high-strength ceramic materials. Those of ordinary skill in the art will appreciate that the mechanism used to set the minimum gap 229 is not a limitation on the scope of the present disclosure.

First and second platens 221 and 222 are formed from an impermeable material such as aluminum. Other impermeable materials, such as steel, may be used, but aluminum has been found to be desirable because the surface roughness of aluminum allows the lost circulation material to adhere to the facing surfaces.

Figure 3:
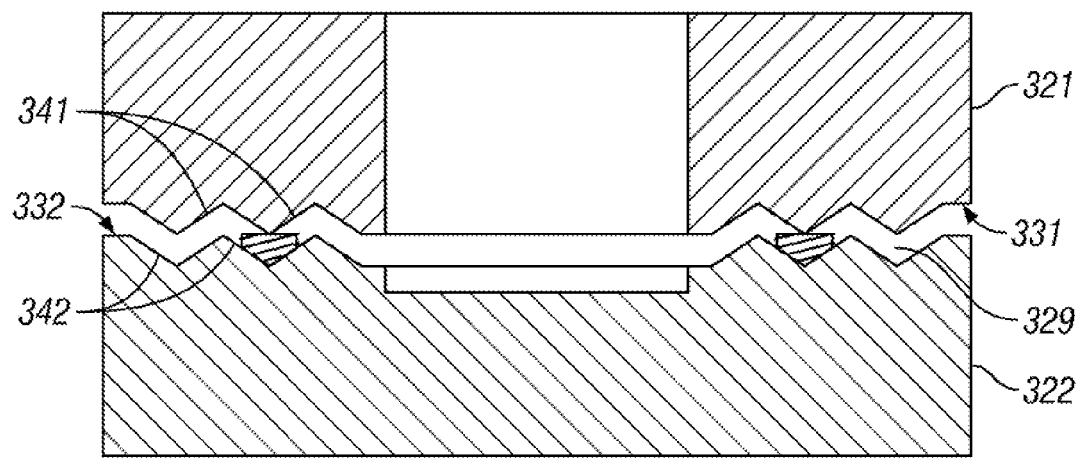
FIG. 3 shows a cross-section view of a pair of opposed platens according to embodiments of the present disclosure.
Figure 4:
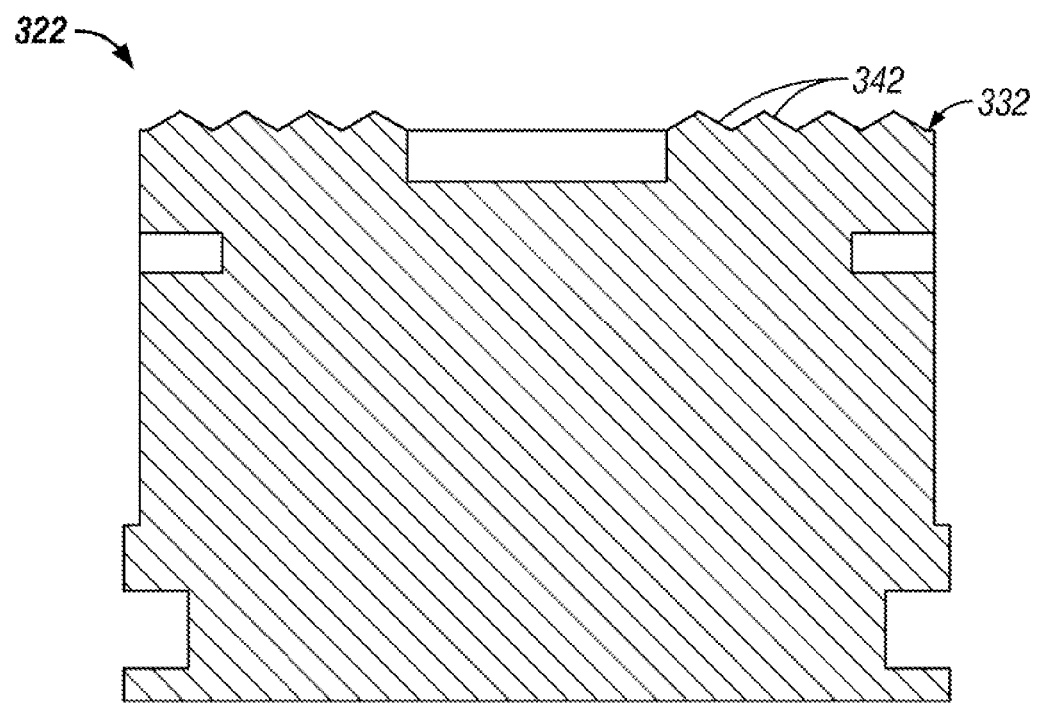
FIG. 4 shows a cross-sectional view of a platen according to embodiments of the present disclosure.
Figure 5:
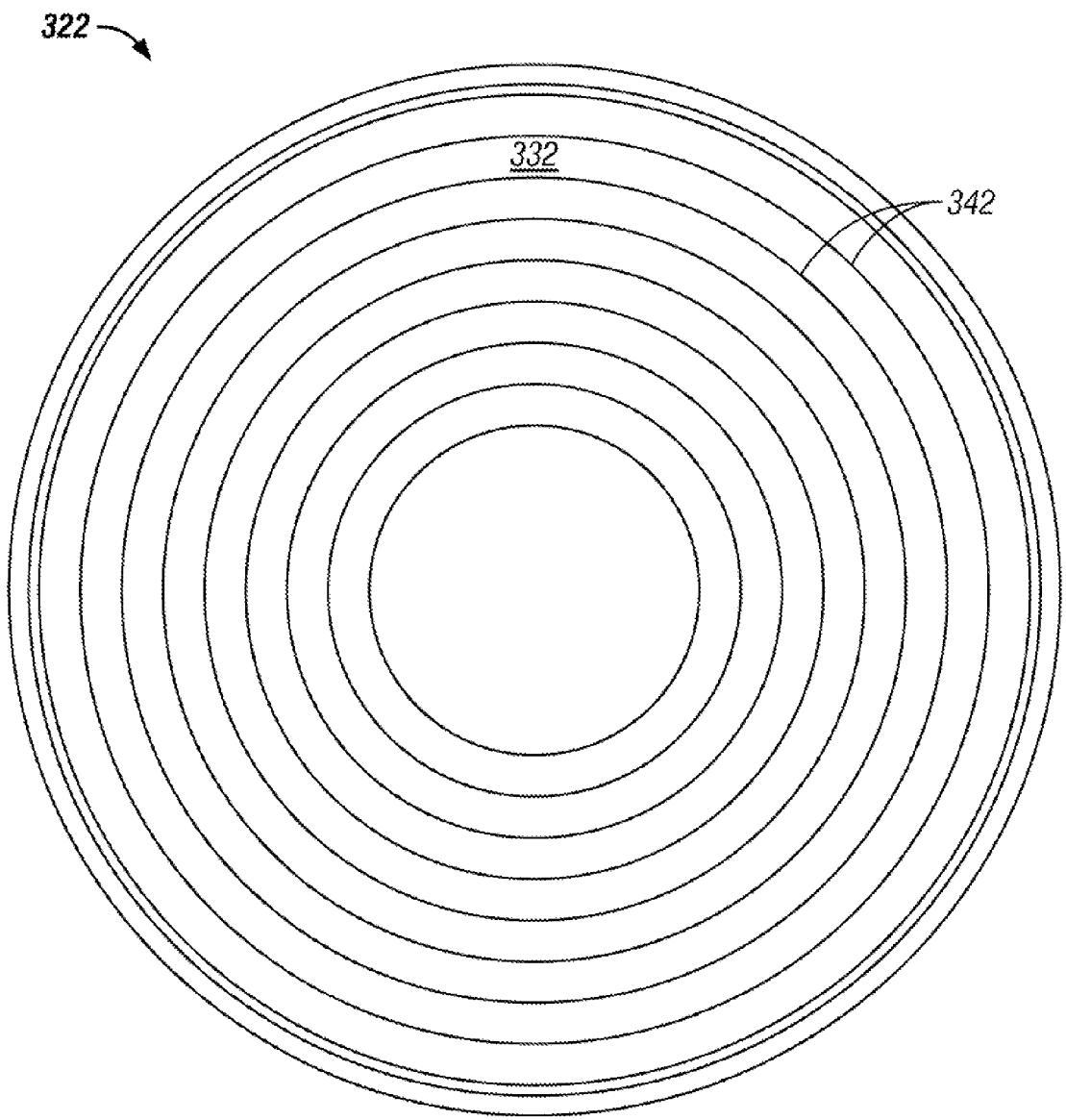
FIG. 5 shows a top view of a the platen of FIG. 4 according to embodiments of the present disclosure.

In one embodiment, the facing surfaces 231 and 232 of the first and second platens 221 and 222 are planar. Referring to FIGS. 3, 4, and 4, in another embodiment, the first platen 321 has a first facing surface 331 with one or more corrugations 341. Second platen 322 has a second facing surface 332 with one or more corrugations 342 corresponding to the corrugations 341 in the first platen 321. As shown in FIG. 3, the corrugations 341 and 342 of each facing surface 331 and 332 may be formed at corresponding, or mating, angles. One of ordinary skill in the art will appreciate that the angles of the corrugations 341 and 342 may be formed at differing angles such that the peaks of corrugations 341 or 342 can abut the valleys of the opposing corrugations 342 or 341 while a gap is formed in the alternative peak/valley combination.

Those of ordinary skill in the art will appreciate that there may be additional geometries of the first and second facing surfaces 331 and 332, such as a single corregation, available without departing from the scope of this disclosure.

Referring again to FIG. 2, vessel 201 is shown including a fluid inlet 250. Vessel 201 also includes a fluid outlet 253.

Operationally, as a drilling fluid is pumped into fluid inlet 350 along path A it contacts platens 221 and 222, representative of a selected formation. A certain portion of the fluid may then be forced out of gap 229, generally following a path of least resistance, along path B, and exit vessel through fluid outlet 253. However, as gap 229 is filled with fluid loss control material, the fluid ceases to exit vessel 201 via fluids outlet 253. As the fluid loss control material seals the gap 229, pressure between the first and second platens 221 and 222 increases. When the pressure between the first and second platens 221 and 222 exceeds the confining pressure (as well as any friction in the system tending to hold the second platen 222 in place, the gap 229 widens and fluid again exits the vessel 201 through the fluid outlet 253.

The fluid exiting through fluid outlet 253 is considered fracture tip fluid loss because gap 229 represents a fracture in a formation. Thus, as fluid loss control materials begin to block the fluid from exiting the fracture tip, thereby sealing the fracture, the substantially constant flow rate from the injected fluid causes the pressure between the first and second platen 221 and 222 to increase.

Operationally, embodiments of the present disclosure may be used to test and determine sealing characteristics of a drilling fluid. Subsequently, the sealing characteristics, and the data obtained from the testing, may be used to optimize a drilling fluid for drilling through a given formation.

Figure 6:
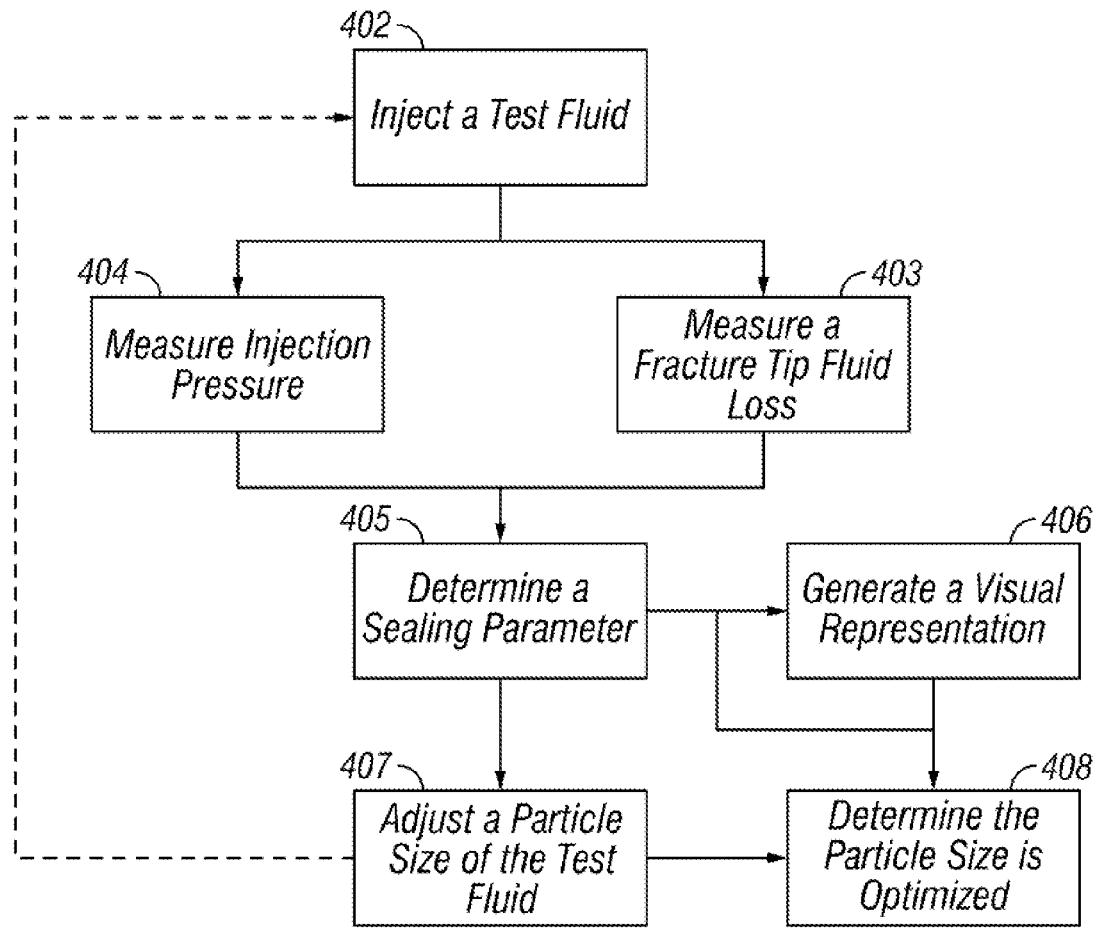
FIG. 6 shows a flow chart of a method for determining sealing characteristics and for optimizing a drilling fluid.

Referring to FIG. 6, a flow chart of a method for determining sealing characteristics and for optimizing a drilling fluid is shown. In this embodiment, a test fluid is injected 402 from a test fluid container. The test fluid may include a water-based or oil-based fluid including fluid loss control material of a known particle size. Examples of fluid loss control materials that may be tested includes sized graphite, barite, calcium carbonate, ground nut, and other fluid loss control material as are known to those of ordinary skill in the art. The test fluid generally contains a known concentration of fluid loss control material and is injected 402 at a constant flow rate into the vessel. Injection 402 continues under known flow rate conditions, and the fluid is substantially continuously injected into a fluid inlet of the vessel. In one embodiment, test fluid is injected at a constant flow rate in the range of 0.25 mL to 1.0 mL/minute. In one embodiment, the test fluid is injected at a constant flow rate of about 0.5 mL/minute.

Inside the vessel, the fluid contacts the platens, and by following a path of least resistance travels through a minimum gap between platens, as described above. As the fluid passes through the minimum gap, the fluid begins to adhere to the sidewalls of the platens, and the fluid loss control material begins to block fluid flow through the gap. However, some of the fluid may pass through fluid outlet and into a collection container. The volume of fluid flowing into the collection container may then be measured 403, and as such, a measured fracture tip fluid loss is determined. The amount of fluid lost through the gap represents a fracture tip fluid loss, as described above, and may be used later in the process for determining sealing properties of fluid loss control material and/or drilling fluids in general.

As the fluid loss control material begins to block fluid flow through the gap, the mud pump pressure required to provide test fluid to the vessel at a constant flow rate increases. The mud pump pressure is measured to help determine the sealing effectiveness and the rapidity of seal development.

As the measurements of fracture tip fluid loss and the mud pump pressure are determined, a data acquisition system, as described above, may be recording and collecting data from the system. Examples of such collected data may include the pressures, back pressures, fluid flow rates, and gap width of the system. This data may later be used to determine, for example, the range of fracture size that can be sealed by a particular fluid loss control material.

After collecting all necessary data, including measuring a fracture tip fluid loss, a sealing parameter is determined 405. Examples of sealing parameters that may be determined for a fluid include, an effective particle size, a fluid loss reduction, and/or a maximum gap width that can be sealed. Those of ordinary skill in the art will appreciate that additional sealing parameters may also be determined that are based on, for example, viscosities of the fluid and/or sealing times.

Still referring to FIG. 6, after a sealing parameter is determined, an operator may conclude the test by outputting and/or visually representing 406 the collected data and/or determined sealing parameters. Specific aspects of the visual representation will be discussed in greater detail below with regard to the Example discussed herein. Generally, however, a visual representation may include numerical, graphical, or pictoral representations of the collected and/or determined data. Such representations may be output to a computer screen, printed on paper, or otherwise stored in a database for further analysis.

In certain embodiments, an operator may decide after determining 405 a sealing parameter that the fluid could be optimized by changing a variable in the drilling fluid. Thus, the operator may adjust 407 a parameter of the fluid and re-run the test. Examples of parameters that the operator may adjust include a viscosity, a flow-rate, a pressure, a back pressure, a fluid loss control fluid particle size, or changing other parameters of the system as would be known to those of skill in the art.

After a parameter of the fluid is adjusted 407, in this embodiment a particle size of a fluid loss control material, the test may be restarted by repeating the injecting 402, the measuring 403, 404, and determining 405 until the fluid is optimized 408. Optimization depends on the conditions an operator may be trying to achieve, however, examples of optimization may include when a drilling fluid seals within a given time interval, under a certain pressure, or under a certain fluid flow rate. Additionally, optimization may include optimizing a specified sealing parameter. Thus, in some embodiments, a fluid loss control material particle size may be optimized for a specified fracture width or in consideration of specific formation porosity.

EXAMPLES

The following examples were used to test a drilling fluid with fluid loss control particles according to the methods and systems disclosed herein:

Example 1

Fracture tests using the systems and methods disclosed herein were focused to evaluate, inter alia, the sealing performance of a cellulosic fluid loss control material. Data was evaluated with respect to test fluid pressure, conduction loss, and fracture size.

Under typical test conditions starting with an initial fracture size of 530 microns, a constant flow rate of test fluid was injected to the vessel. The testing followed in accordance to the methods of testing fluids described in detail above. Briefly, a test fluid was pumped from a test fluid container to a vessel having two opposed platens disposed therein with a minimum initial gap representative of a fracture therebetween. The test fluid continued to flow through the vessel allowing fracture tip fluid to exit the vessel by flowing into a collection container. During the test, the pressures, and other variables effecting the test were recorded by a data acquisition system and transmitted to a computer. The computer then compiled the data and measured a fracture tip fluid loss, a test fluid pressure, a conduction loss, and fracture width. This data was then visually represented as a graph and displayed as described below.

Figure 7:
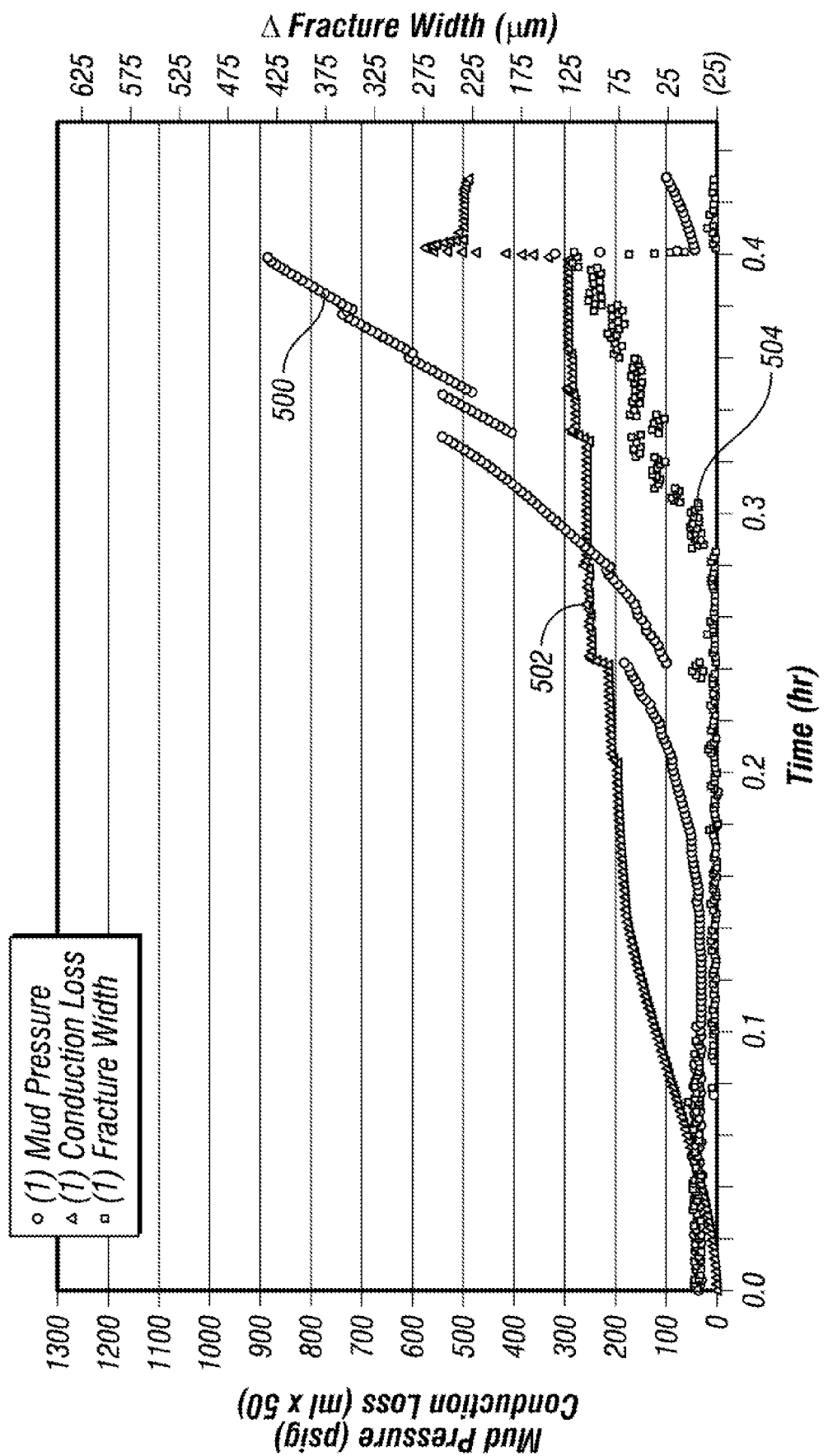
FIGS. 7 and 8 show visual representations of impermeable fracture test data generated according to embodiments of the present disclosure.

Referring to FIG. 7, a visual representation of a the data collected during a test of a fluid in accordance with embodiments of the present disclosure is shown. The following test includes an analysis of test fluid pressure ("mud pressure") 500, mud volume to tip ("conductivity loss") 502, fracture width 504.

Mud pressure 500 may be interpreted as the sealing pressure on the wellbore side of the fracture. As a bridge is formed, mud pressure 500 increases. Fluid pressure may continue to increase until a maximum of approximately 1200 psi, or the maximum operating pressure limit is met. Regarding conductivity 502, the value increases steadily with time as whole mud is lost to the fracture. Once an initial bridge forms, load-off is reduced and the slope of the line should flatten out. This reduction in slope corresponds to the building of a fracture seal and with it a corresponding reduction in fluid lost to the fracture. Referring to the fracture width, 504, as the test fluid pressure builds, and while the fracture seal formed remains in place, the fracture width is held steady (within design parameters) until the seal breaks. A break is indicated by a drop in fluid pressure combined with a minor increase in facture width as the pumps compensate. Upon failure, fracture width 504 returns to the initial point and the mud pressure begins to rise again as a new seal forms.

Example 2

Fracture tests using the systems and methods disclosed herein were focused to evaluate, inter alia, the sealing performance of barite as a fluid loss control material. Data was evaluated with respect to test fluid pressure, conduction loss, and fracture size.

Under typical test conditions starting with an initial fracture size of 280 microns, a constant flow rate of test fluid was injected to the vessel. The testing followed in accordance to the methods of testing fluids described in detail above.

Figure 8:
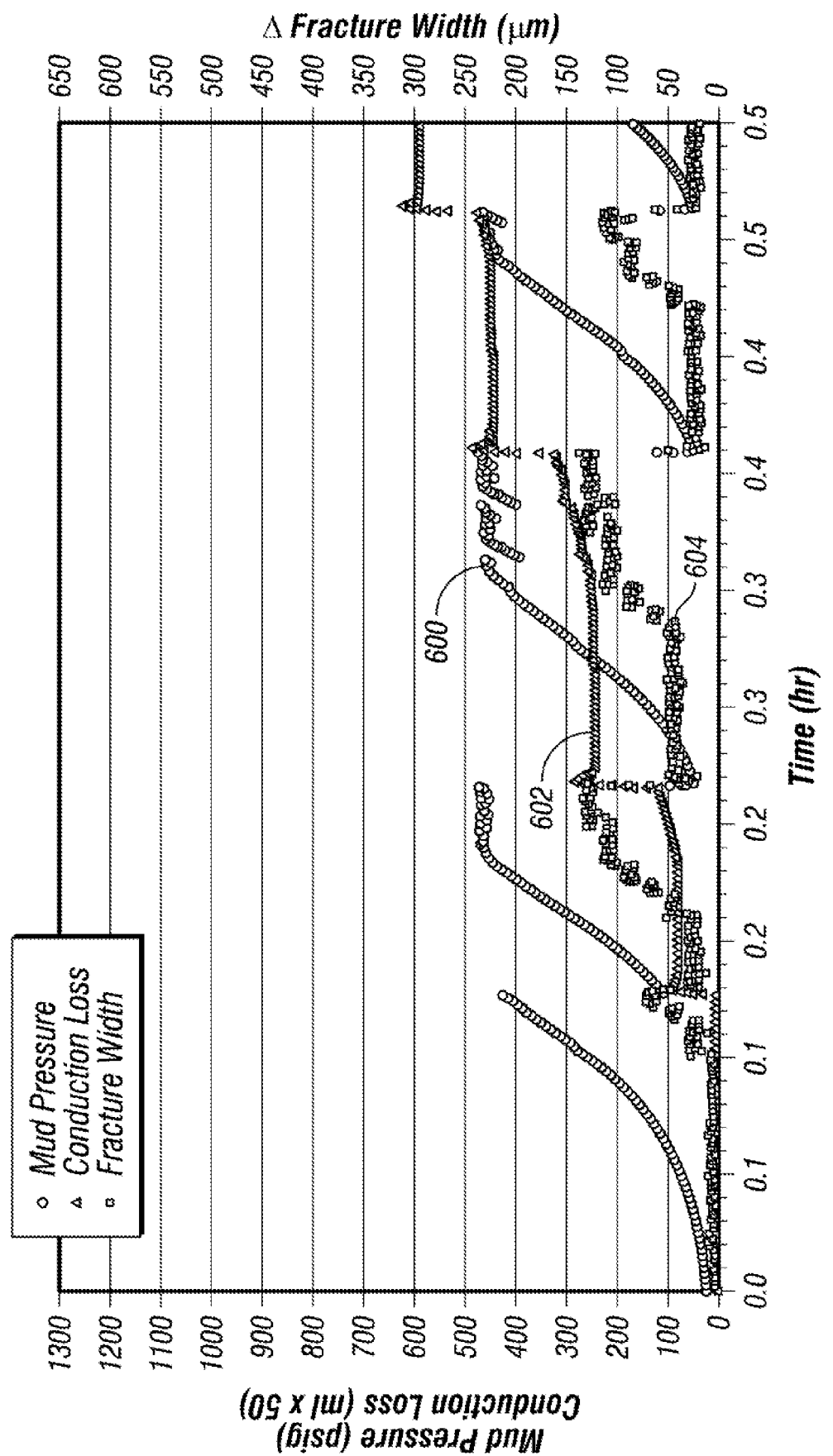

Referring to FIG. 8, a visual representation of a the data collected during a test of a fluid in accordance with embodiments of the present disclosure is shown. The following test includes an analysis of test fluid pressure ("mud pressure") 600, mud volume to tip ("conductivity loss") 602, fracture width 604.

Mud pressure 600 increased relatively quickly at the beginning of the test indicating a fast forming seal was created. As previously discussed regarding conductivity 602, the value increases steadily with time as whole mud is lost to the fracture. Once an initial bridge forms, load-off is reduced and the slope of the line should flatten out. This reduction in slope corresponds to the building of a fracture seal and with it a corresponding reduction in fluid lost to the fracture. Referring to the fracture width, 604, as the test fluid pressure builds, and while the fracture seal formed remains in place, the fracture width is held steady (within design parameters) until the seal breaks. A break is indicated by a drop in fluid pressure combined with a minor increase in facture width as the pumps compensate. Upon failure, fracture width 604 returns to the initial point and the mud pressure begins to rise again as a new seal forms. After multiple increases and decreases in fracture width due to the increased mud pressure, one can see that the barite seal held a change in fracture sealing width of about 125 microns.

Those of ordinary skill in the art will appreciate that the above described example is only one such outcome of a test using systems and methods in accordance with the present disclosure. In other embodiments, the test may include additional visual representations of data and/or data sets compiled by a data acquisition system or computer, and may include a detailed analysis of varied properties of fluid loss control materials.

Advantageously, embodiments of the present disclosure may provide systems and methods for testing and evaluating drilling fluids and fluid loss control materials. Embodiments disclosed herein may advantageously provide methods for assessing the effectiveness of fluid loss control materials in sealing impermeable fractures. Furthermore, the system and methods may inexpensively and rapidly test the sealing effectiveness of various fluid loss control materials as well as provide a way to control and measure changes in fracture width in formation.

Also advantageously, the systems and methods disclosed herein may allow an operator to optimize fluid loss control materials types and concentrations for specific fracture widths, as well as providing an indication of propped width within sealed fractures caused by fluid loss control materials that have been pressed into the fractured.

While the present disclosure has been described with respect to a limited number of embodiments, those skilled in the art, having benefit of the present disclosure will appreciate that other embodiments may be devised which do not depart from the scope of the disclosure described herein. Accordingly, the scope of the disclosure should be limited only by the claims appended hereto.

What is claimed is:

1. An apparatus for testing a drilling fluid comprising:
   a vessel having
      a fluid inlet;
      a fluid outlet; and
      a pair of opposed impermeable platens disposed to create a gap within the vessel;
   a test fluid container containing a test fluid in fluid communication with the fluid inlet;
   a first pump connected to the test fluid container to deliver the test fluid to the vessel via the fluid inlet;
   a sensor associated with the fluid outlet to determine loss of the test fluid from the gap and the fluid outlet;
   a collection container in fluid communication with the fluid outlet; and
   a data acquisition device configured to receive data from at least one of the sensor, the vessel, the test fluid container, and the collection container.

2. The apparatus of claim 1, wherein the vessel further comprises:
a second pump operatively connected to the vessel to apply a constant confining pressure to one of the pair of opposed platens.

3. The apparatus of claim 1, further comprising:
a computer operatively connected to the data acquisition device to interpret the data from at least one of the sensor, the vessel, the test fluid container, and the collection container.

4. The apparatus of claim 1, further comprising:
at least one pump configured to provide a pressure to at least one of the vessel, the test fluid container, and the collection container.

5. The apparatus of claim 4, wherein the at least one pump is operatively connected to the data acquisition device.

6. The apparatus of claim 4, wherein the at least one pump comprises a syringe pump.

7. The apparatus of claim 1, wherein the pair of opposed impermeable platens are separated with a proppant.

8. The apparatus of claim 1, wherein the opposed impermeable platens are separated by at least one set screw.

9. The apparatus of claim 1, wherein the opposed impermeable platens comprise:
a first plate disposed inside the vessel proximate the fluid inlet, wherein the first plate includes a first facing surface;
a second plate disposed inside the vessel, wherein the second plate has a second facing surface proximate the first facing surface of the first plate;
wherein the first facing surface and the second facing surface include at least one corresponding corrugation.

10. The apparatus of claim 1, wherein the opposed impermeable platens are separated by a distance in the range of 0 to 2000 microns.

11. The apparatus of claim 1, wherein the opposed impermeable platens are separated by a distance in the range of 250 to 1000 microns.

12. A method for determining sealing characteristics of a drilling fluid comprising:
injecting a test fluid having a fluid loss control material from a test fluid container to a vessel, the vessel comprising:
a first impermeable platen;
a second impermeable platen;
wherein the two platens are disposed to create a gap; and
measuring a fracture tip fluid loss through the gap.

13. The method of claim 12, further comprising:
determining a sealing parameter based on the fracture tip fluid loss.

14. The method of claim 13, wherein the determining the sealing parameter comprises determining at least one of a rapidity of seal development, fluid loss to fracture tip, and range of fracture size that can be sealed by a fluid loss control material.

15. The method of claim 13, further comprising:
visually representing at least one of a group consisting of a fracture tip fluid loss, a matrix fluid loss, a first sealing parameter, and a second sealing parameter.

16. An apparatus for testing the seal characteristics of a drilling fluid comprising:
a vessel having
a fluid inlet;
a fluid outlet;
a first impermeable platen disposed within the vessel; and
a second impermeable platen disposed within the vessel and opposing the first platen wherein the first platen and the second platen are separated by a predetermined minimum distance;
a test fluid container in fluid communication with the fluid inlet wherein the test fluid container provides a test fluid to the vessel via the fluid inlet;
a collection container in fluid communication with the fluid outlet wherein the test fluid flows between the first platen and the second platen and exits the fluid outlet into the collection container;
a sensor associated with the fluid outlet to sense the test fluid exiting the fluid outlet and provide a signal indicative of a seal characteristic of the test fluid; and
a data acquisition device configured to receive the signal from the sensor and receive data from at least one of the vessel, the test fluid container, and the collection container.

17. The apparatus of claim 16, further comprising
a pump operatively connected to the vessel to apply a constant confining pressure to the second platen; and
wherein the first platen is fixed within the vessel.

18. The apparatus of claim 17, wherein the confining pressure is in the range of 100 to 500 psi.

19. The apparatus of claim 16, wherein the first platen and the second platen are separated by proppant.

20. The apparatus of claim 16, wherein the first platen and the second platen are separated by at least one set screw disposed within the second platen.

21. The apparatus of claim 16, further comprising:
a mud pump operably connected to the test fluid container;
wherein the mud pump supplies mud to the vessel at a flow rate in the range of 0.25 to 1.0 mL per minute.

22. The apparatus of claim 16, further comprising:
a tip pump operably connected to the collection container;
wherein the tip pump applies back pressure in the range of 20 to 30 psi to fluid collected in the collection container.

* * * * *